US005637591A

United States Patent [19]

Ono et al.

[11] Patent Number: 5,637,591

[45] Date of Patent: Jun. 10, 1997

[54] ANTIMICROBIAL AND ANTICOLLAGENASE ACTIVITY OF PHENAZINE-5, 10-DIOXIDE AND DERIVATIVES

[75] Inventors: Mitsunori Ono, Lexington; Y.-S. Edmond Cheng, Wayland; Douglas F. Marks, Jr., Sommerville, all of Mass.; Hiroshi Kataguchi, Hatano, Japan

[73] Assignee: Fuji ImmunoPharmaceuticals Corp., Lexington, Mass.

[21] Appl. No.: 460,649

[22] Filed: Jun. 2, 1995

[51] Int. Cl.$^6$ .................................................. A61K 31/495
[52] U.S. Cl. ......................... 514/250; 514/251; 435/238; 544/347; 544/348
[58] Field of Search ................................ 544/347, 348; 435/238; 514/250, 251

[56] References Cited

U.S. PATENT DOCUMENTS

| | | |
|---|---|---|
| 3,567,728 | 3/1971 | Johnston et al. . |
| 3,594,383 | 7/1971 | Seng et al. . |
| 3,678,051 | 7/1972 | Leimgruber et al. . |
| 3,822,265 | 7/1974 | Leimgruber et al. . |
| 4,948,783 | 8/1990 | Kawai et al. ............................ 514/46 |
| 4,997,830 | 3/1991 | van Winkelhoff et al. ............ 514/197 |
| 5,094,843 | 3/1992 | Mazzanobile et al. .................. 424/52 |
| 5,147,632 | 9/1992 | Pan et al. .................................. 424/54 |

FOREIGN PATENT DOCUMENTS

| | | |
|---|---|---|
| 0205339 | 12/1986 | European Pat. Off. . |
| 0374991 | 6/1990 | European Pat. Off. . |
| 1103137 | 2/1968 | United Kingdom . |
| 1182617 | 2/1970 | United Kingdom . |
| 1232265 | 5/1971 | United Kingdom . |
| 1285010 | 8/1972 | United Kingdom . |

OTHER PUBLICATIONS

I.B. Lamster et al. (1993) "Current Status of Tests for Periodontal Disease," *Adv. Dent. Res.*;7(2):182–190.

Lillian V.H. Moore et al. (1993) "Periodontal Microflora of HIV Positive Subjects With Gingivitis or Adult Periodontitis," *J. Periodontol*; 64(1):48–56.

W.E.C. Moore et al. (1993) "Investigation of the Influences of Puberty, Genetics, and Environment on the Composition of Subgingival Periodontal Floras," *Infection and Immunity*;61(7):2891–2898.

Arie J. van Winkelhoff et al. (1993) "Occurrence and Association With Disease," *Biology of the Species Porphyromonas Gingivalis*; Chapter 2:33–42.

Anne Tanner et al. (1993) "Oral and Dental Infections with Anaerobic Bacteria: Clinical Features, Predominant Pathogens, and Treatment," *Clinical Infectious Diseases*; 16(Suppl 4):S304–9.

R.T. Evans et al. (1992) "Periodontopathic Potential of Two Strains of *Porphyromonas Gingivalis* in Gnotobiotic Rats," *Archs. Oral Biol.*;37(10):813–819.

Lars G. Petersson et al. (1992) "Antimicrobial Effect of a Dental Varnish, In Vitro," *Swed Dent. J.*;16:183–189.

D. Wray et al. (1992) "Periodontal Bone Loss in Mice Induced by Different Periodontopathic Organisms," *Archs. Oral Biol.*;37(6):435–438.

Lars A. Christersson et al. (1991) "Dental Bacterial Plaques –Nature and Role in Periodontal Disease," *J. Clin. Periodontol*;18:441–446.

Bjarne Klausen et al. (1991) "Periodontal Bone Level and Gingival Proteinase Activity in Gnotobiotic Rats Immunized With *Bacteroides Gingivalis*,"*Oral Microbiol Immunol*;6:193–201.

Caroline A. Genco, et al. (1991) "A Novel Mouse Model To Study the Virulence of and Host Response to *Porphyromonas (Bacteroides) Gingivalis*," *Infection and Immunity*;59(4):1255–1263.

Robert J. Genco, (1991) "Using Antimicrobial Agents To Manage Periodontal Diseases," *JADA*; 122:31–38.

J.M. Goodson et al. (1991) "Multicenter Evaluation of Tetracycline Fiber Therapy. III. Microbiological Response," *J. Periodont. Res.*;26:440–451.

M.F.J. Maiden et al. (1991) "Tetracycline Fiber Therapy Monitored by DNA Probe and Cultural Methods," *J. Periodont. Res.*;26:452–459.

I. Magnusson et al. (1991) "Clinical, Microbiological and Immunological Characteristics of Subjects With Refractory Periodontal Disease," *J. Clin. Periodontal*;18:291–299.

W.E.C. Moore et al. (1991) "The Microflora of Periodontal Sites Showing Active Destructive Progression," *J. Clin. Periodontal*;18:729–739.

A.J. van Winkelhoff et al. (1991) "Microbiology in the Management of Destructive Periodontal Disease," *J. Clin. Periodontal*;18:406–410.

Stefan Renvert et al. (1990) "Effect of Root Debridement on the Elimination of *Actinobacillus Actinomycetemcomitans* and *Bacteriodes Gingivalis* from Periodontal Pockets," *J. Clin. Periodontol*;17:345–350.

J.P. Rodenburg et al. (1990) "Occurrence of *Bacteroides Gingivalis, Bacteroides Intermedius* and *Actinobacillus Actinomycetemcomitans* in Severe Periodontitis in Relation to Age and Treatment History," *J. Clin. Periodontal*; 17:392–399.

Jergen Slots et al. (1990) "Antibiotics in Periodontal Therapy: Advantages and Disadvantages, " *J. Clin. Periodontal;* 17:479–493.

Joseph J. Zambon et al. (1990) "Studies of the Subgingival Microflora in Patients With Acquired Immunodeficiency Syndrome," *J. Periodontol;* 61:699–704.

(List continued on next page.)

*Primary Examiner*—Hoa Van Le
*Attorney, Agent, or Firm*—Testa, Hurwitz & Thibeault, LLP

[57] ABSTRACT

Disclosed are chemical agents with unexpected antimicrobial activity against the microbes, especially *Porphyromonas gingivalis*, known to be important in the cause and progression of gingivitis, periodontitis, and destruction of hard and soft oral tissues leading to tooth loss. The agents have additional unexpected anticollagenase activity useful in the direct mitigation of tissue damage. The agents can be formulated to produce various compositions and dental implements useful in management of peridental diseases, particularly those involving infection with certain gram-negative anaerobes.

13 Claims, No Drawings

OTHER PUBLICATIONS

Thomas A. Dahl et al. (1989) "Comparison of Killing of Gram–Negative and Gram–Positive Bacteria by Pure Singlet Oxygen," *Journal of Bacteriology;*171(2):2188–2194.

A.J. van Winkelhoff et al. (1989) "Metronidazole Plus Amoxycillin in the Treatment of *Actinobacillus Actinomycetemcomitans* Associated Periodontitis," *J. Clin. Periodontol;*16:128–131.

Anne D. Haffajee et al. (1988) "Effect of Modified Widman Flap Surgery and Systemic Tetracycline on the Subgingival Microbiota of Periodiontal Lesions," *J. Clin. Periodontol;* 15:255–262.

T.E. Van Dyke et al. (1988) "Refractory Periodontitis: Mixed Infection with *Bacteroides Gingivalis* and Other Unusual *Bacteroides* Species," *J. Periodontol;*59:184–189.

Jong Daé Kim et al. (1987) "Synthesis and Antimicrobial Activity of Phenazine Derivatives(I)," *Journal of Korean Chemical Society;*31(5):464–470.

W.E.C. Moore et al. (1987) "Microbiology of Periodontal Disease," *Journal of Periodontal Research;*22:335–341.

A.J. van Winkelhoff et al. (1987) "Microbial Succession in Recolonizing Deep Periodontal Pockets After a Single Course of Supra–and Subgingival Debridement," *J. Clin. Periodontal;*15:116–122.

G.G. Rosling et al. (1986) "Topical Antimicrobial Therapy and Diagnosis of Subgingival Bacteria in the Management of Inflammatory Periodontal Disease," *J. Clin. Periodontol;*13:975–981.

A.J. van Winkelhoff et al. (1986) "Black–Pigmented *Bacteroides* and Motile Organisms on Oral Mucosal Surfaces in Individuals With and Without Periodontal Breakdown," *Journal of Periodontal Research;*21:434–439.

P.J. Baker et al. (1985) "Antibiotic Susceptibility of Anaerobic Bacteria from the Human Oral Cavity," *Journal of Dental Research;*64(10):1233–1244.

Pamela J. Baker et al. (1983) "Minimal Inhibitory Concentrations of Various Antimicrobial Agents for Human Oral Anaerobic Bacteria," *Antimicrobial Agents and Chemotherapy;*24(3):420–424.

M.L. Edwards et al. (1976) "Formyl Substituted Phenazine 5, 10–Dioxides," *J. Heterocyclic Chem.;*13:653–656.

ANTIMICROBIAL AND ANTICOLLAGENASE ACTIVITY OF PHENAZINE-5, 10-DIOXIDE AND DERIVATIVES

BACKGROUND OF THE INVENTION

Inflammation of the soft tissues (gingivae) around teeth is referred to as gingivitis, and may be caused by microbial infection. In the case of progressive infection, direct microbial actions as well as the production of tissue-destructive enzymes such as collagenase, with or without stimulation of host tissue-destructive enzyme activity by the infectious agents, can lead to destruction of supporting tissues around the teeth, a condition referred to as periodontitis (Klausen et al., 1991). The subgingival microbiota associated with these peridental conditions may be comprised of multiple species, and may change during the course and progression of these dental infections. Gram-negative anaerobic bacteria, in particular, are known to play an essential role.

Refractory periodontitis and gingivitis patients, who often suffer from specific infections, are prime candidates for antimicrobial therapy. Unfortunately, the results of most published clinical studies on antibiotic periodontal therapy are ambiguous, primarily because of issues related to susceptibility of causative pathogens to the treatment choice (Slots and Rams, 1990). In addition, few antimicrobial agents have been identified which are active against anaerobic bacteria, and still fewer have activity against gram-negative anaerobic bacteria (e.g., U.S. Pat. No. 4,997,830; Baker et al., 1983). Further, species involved in peridental infections, such as Actinobacillus actinomycetemcomitans and Porphyromonas gingivalis (formerly Bacterioides gingivalis), are refractory to conventional therapies, including chemotherapies (e.g., Tanner and Stillman, 1993; U.S. Pat. No. 4,997,830).

Some of the pathogens involved in peridental infections, such as P. gingivalis, both produce tissue-destructive enzymes such as collagenase and induce the production of collagenolytic enzymes by the host tissues (Evans et al., 1991). By attacking the structural protein collagen, this activity mitigates the structural integrity of the peridental tissues, promoting the destruction of these tissues and loss of alveolar support. This activity therefore directly contributes to the development and progression of periodontal disease, leading to bone loss and possibly tooth loss.

There is a strong association between the eradication of ineffective microorganisms and the success of treatment of dental infections such as gingivitis and periodontal disease. Current therapies for peridental infection include the debridement of infected sites and surgical intervention accompanied by antimicrobial therapy.

Penicillins in general are highly effective antimicrobial compositions against anaerobic bacteria. Some penicillins, such as Amoxicillin, have antimicrobial activity against anaerobic bacteria and some gram-negative bacterial species. Nevertheless, both Penicillin G and Amoxicillin have been shown to be ineffective against bacterial species important in peridental infections, such as P. gingivalis.

Tetracyclines are impressively broad spectrum antimicrobial agents, with activity against a wide range of bacterial and non-bacterial species. However, tetracyclines have a number of disadvantages relative to use in dental medicine which are related to their bacteriostatic mechanism of action and broad spectrum activity. For example, the rapid emergence of bacterial strains which are resistant to tetracyclines and the occurrence of overgrowth of unsusceptible pathogens, such as Candida, during treatment constitute serious limitations to the use of this class of antimicrobials in the treatment or prevention of dental infections leading to tooth loss.

Short term treatment of peridental infection with tetracyclines is often ineffective, or can result in the suppression of the peridental infection during treatment and the subsequent recurrence of infection following cessation of treatment. Longer term treatment (e.g., 3 weeks) has even been shown to increase the growth of potential pathogens via the development of bacterial resistance to tetracyclines and the overgrowth of unsusceptible pathogens. (Slots and Rams, 1990). The broad spectrum of activity of tetracyclines can result in superinfection of the diseased tissue by bacteria which are unsusceptible to its antimicrobial action, and can also result in opportunistic infection of healthy tissues. Prolonged or frequent treatment courses with broad spectrum antimicrobials enable superinfecting organisms to persist in the subgingival microbial community over extended periods of time, contributing to therapeutic failure (i.e., refractory infection). Opportunistic pathogens may also give rise to systemic complications (Slots and Rams, 1990).

The spectrum of antimicrobial effectiveness of currently used therapeutic compounds is summarized below.

| Antimicrobial Agent | Activity Against Anaerobes | Activity Against Gr– | Activity Against Gr– Anaerobes | Activity against A. act and/or P. gin |
|---|---|---|---|---|
| Clindamycin | + | – | – | N/A[1] |
| Metronidazole | + | ± | ± | ineffective[2] |
| 2$^d$-generation Cephalosporins | + | ± | N/A | none described |
| Penicillin G | + | – | N/A | ineffective[3] |
| Amoxicillin | + | + | ± | ineffective[2] |
| Tetracyclines | + | + | + | partially effective[4] |

[1]N/A = not applicable, by limitations in the spectrum of activity.
[2]US 4,997,830
[3]Wadsworth et al., p. 114–5.
[4]The current standard of care, used as reference standard in the instant application.

Additional limitations in dental practice include the tendency of tetracyclines to bind calcium, which can lead to bone and tooth discoloration and dysgenesis. These agents are thereby contraindicated for use in children and pregnant women. Thus, tetracyclines are unsuitable for the treatment of juvenile periodontitis or the forms of gingivitis associated with pregnancy.

The limitations and disadvantages described above for the currently used antimicrobial agents expose the continued need for effective treatment of these dental infections and the discovery and development of antimicrobial agents with activity against the etiological microbes specifically. In order to obviate some of the problems associated with currently employed antimicrobial therapies, such agents ideally should exhibit relatively narrow spectra of activity, while being effective agents against some or all of the relevant oral pathogens.

It is one object of this invention to provide antimicrobially effective compositions having narrow spectra of activity for the treatment of peridental infection. It is another object of this invention to provide a method for treating peridental infections with antimicrobially effective compositions which are active against a narrow spectrum of bacteria. It is a further objective of this invention to provide a method for treating gram-negative anaerobic bacterial infections with compositions that are effective against a narrow spectrum of bacteria. Such antimicrobial agents would also be useful for many other purposes, for example, as an antibacterial agent for in vitro cell culture, a pharmaceutical preservative, an industrial preservative (for example in dyes), and an industrial antibacterial additive to cleaning solutions.

SUMMARY OF THE INVENTION

Phenazine-5,10-dioxide, and substituted derivatives thereof, have been discovered to have antimicrobial action against gram-negative obligate or facultative anaerobic bacteria. Phenazine-5,10-dioxides also have been discovered to have an anti-collagenase activity which mitigates the tissue destructive effects of the collagenase enzymes released by gram-negative anaerobic bacteria and host tissues. Phenazine-5,10-dioxide, and substituted derivatives thereof, also have been discovered to be therapeutically useful in the treatment of gram-negative, anaerobic bacteria infections, and are especially useful for the treatment of peridental infections. Anti-collagenase activity is not required for antimicrobial action, and generally is not an activity associated with antimicrobial agents. Thus, the anti-collagenase activity of phenazine-5,10-dioxide compounds provides a separate and distinct therapeutic benefit for the treatment of peridental disease by directly inhibiting collagenase-mediated tissue destruction involved in gingivitis and periodontal disease which accompanies the antimicrobial activity in treatment of the underlying bacterial infection.

In one aspect, the invention comprises methods of use for a pharmaceutically active composition of a phenazine-5,10-dioxide compound having the formula

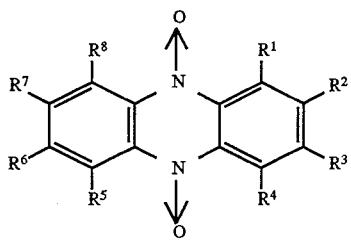

wherein $R_1$, $R_2$, $R_3$, $R_4$, $R_5$, $R_6$, $R_7$, and $R_8$ are independently H, $NH_2$, alkyl having 1–12 carbon atoms, lower alkyl amino, lower alkoxy, hydroxy, chloro, bromo, fluoro, iodo or a pharmaceutically acceptable salt thereof. Two of $R_1$, $R_2$, $R_3$, and $R_4$ may be joined by an amino alkylene chain. In each combination the phenazine-5,10-dioxide is not 2,3-dihydroxyphenazine-5,10-dioxide.

In currently preferred embodiments at least $R_1$, $R_5$, $R_7$, and $R_8$ are hydrogen, and $R_2$, $R_3$, $R_4$, and $R_6$, are independently H, $NH_2$, alkyl having 1–12 carbon atoms, lower alkyl amino, lower alkoxy or hydroxide, wherein two of $R_2$, $R_3$, and $R_4$ may be joined by an amino alkylene or other chain forming a heterocyclic ring.

The lower alkyl amino may be methylamine, ethylmine, n-propylamine, isopropylamine, n-butylamine, or t-butylamine. The lower alkoxy may be methoxy, ethoxy, n-propoxy, isopropoxy, n-butoxy, or t-butoxy.

In another aspect of the invention the phenazine-5,10-dioxide compound is phenazine-5,10-dioxide; 2-aminophenazine-5,10-dioxide; 2-methylphenazine-5,10-dioxide; 2-hydroxyphenazine-5,10-dioxide; or 3,4-imminopropylphenazine-5,10-dioxide.

In another aspect, the invention provides a method of treating peridental infection by administering to an organism an antimicrobially effective amount of the phenazine-5,10-dioxide compound having the formula presented above in admixture with a pharmaceutically acceptable carrier. The peridental infection can be treated systemically by parenteral injection or oral ingestion. The peridental infection also can be treated topically by administering to the oral cavity an oral rinse solution, a gingival paint, a sublingual paste, a dentifrice, a sustained released oral lozenge, a loaded dental floss fiber, or loaded polymer fibers.

Another aspect of the present invention comprises a method of treating gram-negative anaerobic infection by administering to an organism topically or systemically an antimicrobially effective amount of phenazine-5,10-dioxide compound having the formulae shown above.

In still another aspect, the invention comprises a dental implement impregnated with a phenazine-5,10-dioxide compound for treating peridental infection. The dental implement comprises an implement for contact with teeth which is impregnated with an antimicrobially effective amount of phenazine-5,10-dioxide compound having the formula presented above. The dental implement can be impregnated fibers including dental floss and polymer fibers which are used in drag therapy. The dental implement can also be a fluoride toothpaint, a subgingival paste, or a dentifrice. The dental implement can be also a dental tool used for stimulating the periodontal tissue such as a toothpick or rubber tip.

The invention will be understood further from the following description and claims.

DETAILED DESCRIPTION OF THE INVENTION

The methods of the present invention generally comprise administering to an individual afflicted with a peridental disease or a gram-negative anaerobic bacterial infection an amount of a phenazine-5,10-dioxide compound which is sufficient to reduce or ameliorate the symptoms of the disease and/or effectively eradicate the bacterial infection.

Compounds which are particularly effective for this purpose include, substituted derivatives of phenazine-5,10-dioxide (N,N'-dioxides of phenazine), which are described in detail below. The term "phenazine-5,10-dioxide(s)" or "phenazine-5,10-dioxide compound" will be used herein to include phenazine-5,10-dioxide and substituted derivatives thereof.

The language "peridental infections" or "peridental diseases" is intended to include periodontitis, gingivitis and other bacterial infections of the oral cavity and peridental tissues.

The language "treating peridental infections" or "treating gram-negative bacterial infections" is intended to include prevention of the disease/infection, amelioration and/or arrest of a preexisting disease/infection condition, and the elimination of a preexisting disease/infection. The phenazine-5,10-dioxides described herein have both curative and prophylactic effects in disease development and progression.

The language "therapeutically effective amount" is intended to include the amount of phenazine-5,10-dioxide sufficient to prevent onset of diseases of the peridental tissue and/or disease symptoms caused by gram-negative bacterial infection, or to significantly reduce progression of such diseases in the subject being treated. A therapeutically effective amount can be determined on an individual basis and will be based, at least in part, on consideration of the severity of the symptoms to be treated. Further, the effective amounts of the phenazine-5,10-dioxide compound may vary according to age, sex, and weight of the subject being treated. Thus, a therapeutically effective amount of the phenazine-5,10-dioxide compound can be determined by one of ordinary skill in the art employing such factors described above using no more than routine experimentation in clinical management. See also, the publications of the National Committee for Clinical Laboratory Standards, for example, Methods for Antimicrobial Susceptibility Testing of Anaerobic Bacteria", 2nd Edition, vol. 9, no. 10. Approved Standard, NCCLS Publication M11-A2, NCCLS, Villanova, Pa., 1990, the disclosure of which is incorporated herein by reference.

In the preferred embodiments of each aspect of the present invention, the composition of substituted phenazine-5,10-dioxide compound includes a pharmaceutically acceptable carrier substance for topical application, oral ingestion or parenteral injection. The language "pharmaceutically acceptable carrier" is intended to include substances capable of being co-administered with the phenazine-5,10-dioxide compound and which allows the compound to perform its intended function of preventing, ameliorating, arresting or eliminating a peridental disease or gram-negative, anaerobic bacterial infection. Examples of pharmaceutically acceptable carriers are commercially available inert gels or liquids. Useful gels include the compound, a base selected from an oleaginous base, water, or emulsion-suspension base, and a gelling agent, such as hydroxypropyl cellulose, acrylic acid polymers, and the like. Liquids include emulsions, solutions, and suspensions, such as those listed in Tables 8 and 9. Pharmaceutically acceptable salts, which are recognized in the art, may also be used for the preparation of phenazine-5,10-dioxide compounds. The term "pharmaceutically acceptable salt" is intended to include act-recognized pharmaceutically acceptable salts. Typically these salts are capable of being hydrolyzed under physiological conditions. Examples of such salts include sodium, potassium, and hemisulfate and organic molecules. Additionally, a carrier having effective bioavailability should be used in preparations of the compound for oral ingestion.

The term "subject" is intended to include living organisms susceptible to gram-negative, anaerobic bacterial infections and peridental diseases. Examples of subjects include humans and animals such as dogs, cats, horses, cows, goats, rats and mice.

A therapeutically effective amount of a phenazine-5,10-dioxide compound comprises an amount of the phenazine-5,10-dioxide such that the growth of susceptible gram-negative, anaerobic microorganisms is mitigated during the normal duration of therapy (generally within about 3 weeks). Susceptible gram-negative anaerobic microorganisms include those bacteria involved in gingivitis periodontitis and other peridental diseases. The amount to be administered will depend upon the physical-chemical characteristics of the individual compounds, the route of administration, the bioavailability of the agents by the chosen route, and the potency of the individual agents against the etiological organism(s). The amounts of phenazine-5,10-dioxide compound incorporated into the formulation of the present invention is not critical; the concentration should only be in a range sufficient to permit ready application of the formulation in an amount which will deliver the desired amount of phenazine-5,10-dioxide compound. In general, the dose would reasonably be expected to range between 0.001–1 g per adult human per administration for systemic use.

The amount for topical use for treatment of peridental infections would reasonably be expected to depend upon the form of the application, and would conform with pharmaceutical industry standards for incorporation into, for example, oral rinse solutions, gingival paints, sublingual pastes, dentifrices, sustained release oral lozenges (solid or gelatinous lozenges), loaded dental floss fibers, or polymer fibers useful to drag-fiber therapy. Such topical applications can be prepared for administration by trained dental workers, or self-administration by the subject.

In one preferred embodiment of the invention, treatment of peridental infections includes administration of phenazine-5,10-dioxide compound regimens adapted for use as monotherapies, or in conjunction with conventional antimicrobial therapies, or in conjunction with planing, scaling or other mechanical or surgical debridement procedures. Administration of phenazine-5,10-dioxide compound regimens also can be effectuated by a dentist- or dental professionist. Finally, administration of phenazine-5,10-dioxide compound regimens can be patient self-effectuated, either as over the counter (OTC) preparations or as prescribed formulations.

The structure of phenazine-5,10-dioxide is shown below. The positions at which the compound can be derivatized are shown with the nomenclature numbers positioned around the periphery of the compound.

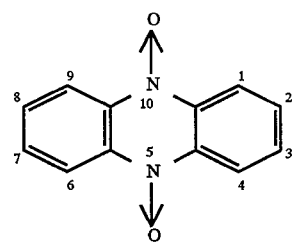

Phenazine-5,10-dioxide

The arrows indicate a resonance structure. In several preferred embodiments, the instant invention relates to N,N'-dioxides of phenazine having one or more substitutions at the locations identified as $R_1$–$R_8$ in the following diagram.

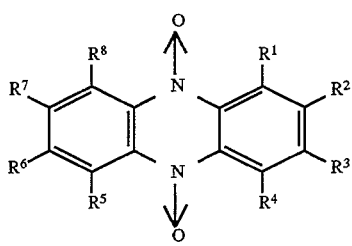

The synthesis and derivatization of phenazine-5,10-dioxide compounds has been previously described. See, for example, U.S. Pat. Nos. 3,822,265, 3,678,051, 3,567,782 and 3,594,383, each of which is incorporated herein by reference. The following example of a synthesis and purification of a phenazine-5,10-dioxide derivative is exemplary and is not intended to be limiting.

The identities of several substitutions are summarized in the following chart, and the structural formula of each compound is provided in the following diagrams.

| Compound | R2 | R3 | R4 | R6 |
|---|---|---|---|---|
| 2-amino,7-methoxyphenazine-5,10-dioxide | $NH_2$ | H | H | $OCH_3$ |
| phenazine-5,10-dioxide | H | H | H | H |
| 2-methylphenazine-5,10-dioxide | $CH_3$ | H | H | H |
| 2-hydroxyphenazine-5,10-dioxide | OH | H | H | H |
| 2,3-dihydroxyphenazine-5,10-dioxide | OH | OH | H | H |
| 2-aminophenazine-5,10-dioxide | $NH_2$ | H | H | H |
| 2-hydroxy-3,4-iminopropylphenazine-5,10-dioxide | OH | —N=CH—CH=CH— | | H |

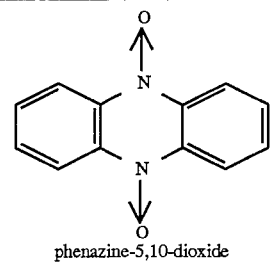

phenazine-5,10-dioxide

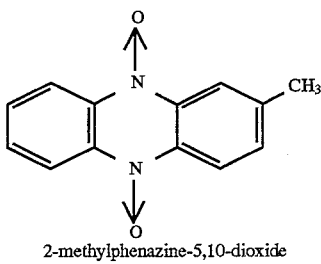

2-methylphenazine-5,10-dioxide

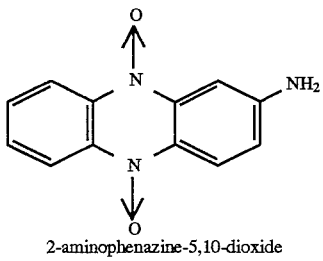

2-aminophenazine-5,10-dioxide

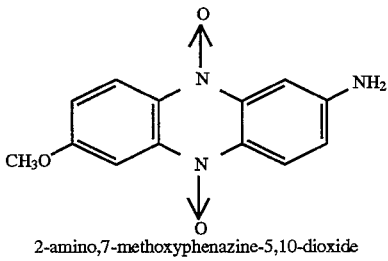

2-amino,7-methoxyphenazine-5,10-dioxide

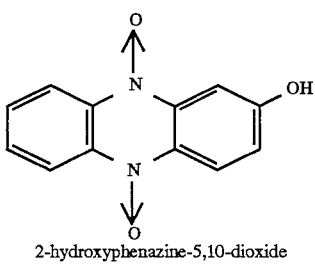

2-hydroxyphenazine-5,10-dioxide

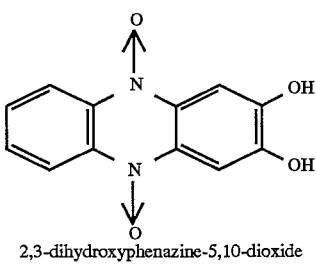

2,3-dihydroxyphenazine-5,10-dioxide

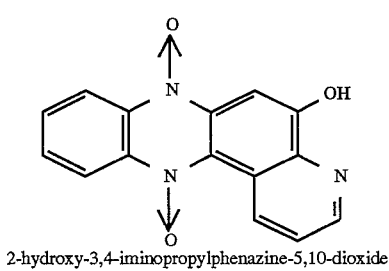

2-hydroxy-3,4-iminopropylphenazine-5,10-dioxide

EXAMPLE 1

Synthesis and Purification of 7-methoxy-2-aminophenazine-5,10-dioxide (A) Preparation of 3-nitro-4-acetylamino-1-methoxybenzene A 300 mL flask equipped with stirring bar, thermometer, and dropping funnel was charged with 4-acetylaminomethoxybenzene (25 g, 0.152 mole), 55 mL of acetic acid (0.96 mole), 18.8 mL of acetic anhydride (0.2 mole), and 86.2 mL of distilled water. Fuming nitric acid (15.2 mL) was then added dropwise via the dropping funnel at a rate such that the internal temperature was maintained at 45° C. After the addition was complete, the reaction mixture was maintained at 45° C. for 1 h and cooled to room temperature to produce the precipitation of a yellow solid. The precipitated solid was filtered, washed with ice water several times, and recrystallized in ethanol to give 3-nitro-4-acetylamino-1-methoxybenzene (23.9 g, 75% yield, m.p. 116°–117° C.).

(B) Preparation of 3-nitro-4-amino-anisole

To a 200 mL flask equipped with reflux condenser, thermometer, and stirring bar was added 3-nitro-4-acetylamino-1-methoxybenzene (22 g., 0.11 mole), 34.4 mL of 10% aqueous alcoholic sodium hydroxide. The stirring mixture produced the precipitation of red solid over 3 hours. The precipitate was filtered and washed with ice water and recrystallized from MeOH to give 3-nitro-4-amino-anisole (16.8 g., 95% yield, m.p. 123°–124° C.). Spectral characterizations of these materials were identical with literature information. Kim, et al., *J. Korean Chem. Soc.*, 1987, 31: 464–470.

(C) Preparation of 4-Methoxy-2-nitrophenylazide

To a 0° C. solution of 4-methoxy-2-nitroaniline (15.28 g, 90.9 mmol) in 36 mL of distilled water was added 21 mL of concentrated hydrocholoric acid dropwise maintaining the reaction temperature below 5° C. A solution of sodium nitrite (6.22 g, 90.2 mmol) in 22 mL of distilled water was added via addition funnel maintaining the reaction temperature below 5° C. The brown solution was stirred for one hour and then filtered to collect the filtrate which was diluted with 200 mL distilled water. A solution of sodium azide (5.89 g, 90.63 mmol) in 22 mL of distilled water was added dropwise producing a rapidly expanding yellow foam. After gas evolution had ceased, the crude product was filtered and recrystallized from methanol to give 14.98 g (85% yield) of azide as yellow needles (m.p. 76°–78° C.). $R_f$ 0.32 in 20% ethyl acetate/hexane; IR (CHCl$_3$) 2124, 1535, 1497, 1292, 1235; $^1$H NMR (CDCl$_3$) δ 7.44 (d, J=2.8 Hz, 1H), 7.23 (d, J=8.8 Hz, 1H), 7.17 (2 d, J=2.8 Hz, J=9.1 Hz, 1H), 3.85 (s,3H).

(D) Preparation of 6-Methoxybenzenefuroxan

A mixture of the 4-methoxy-2-nitrophenylazide (5.06 g, 26.1 mmol) and 7.8 mL of fleshly distilled toluene was heated to 110° C. for three hours and then cooled to 95° C. and stirred for an additional two hours. The toluene was removed in vacuo to give a brown solid. The crude product was recrystallized from methanol to yield 3.35 g (77% yield) of benzofuroxan as orange-brown crystals (m.p. 114°–115° C.). $R_f$ 0.30 in 20% ethyl acetate/hexane. $^1$HNMR (CDCl$_3$) δ 6.19 7.45 (m, 3H), 3.89 (s, 3H).

(E) Preparation of 7-Methoxy-2-aminophenazine-5,10-dioxide

To a solution of 6-methoxybenzenefuroxan (3.33 g, 20.0 mmol), 4-aminophenol (2.17 g, 19.9 mmol) in 25 mL of ethanol was added 15 mL of a 0.25M solution of NaOH in distilled water. The black slurry was stirred at room temperature for 40 hours then pipelied into a solution of 1130 mL ice water and 25 mL of a 5N solution of hydrochloric acid in distilled water. The solution was stirred at room temperature for one hour to insure thorough mixing. The acidic solution was then filtered to give a sticky, black solid. This was triturated with hot methylene chloride and filtered. The solid was washed thoroughly with methylene chloride, collected and stored as tile ammonium hydrochloride salt (65% yield). $^1$H NMR (d$_6$-DMSO) δ 8.38 (d, J=9.6 Hz, 1H), 831 (d, J=9.4 Hz, 1H), 7.78 (d, J=2.5 Hz, 1H), 7.48 (2 d, J=2.5 Hz, J=9.6 Hz, 1H), 7.38 (d, J=2.1 Hz, 1H), 7.33 (2d, J=2.1 Hz, J=9.4 Hz, 1H), 6.67 (br,2H), 3.97 (s, 3H).

(F) Purification of 7-Methoxy-2-aminophenazine-5,10-dioxide

Upon dissolving in methanol, the hydrochloride salt was eluted through a basic ion exchange resin (Amberlite IR-45) with anhydrous methanol. Fractions were combined and the methanol was removed under reduced pressure. The reddish-purple residue was heated in methanol/methylene chloride, cooled to 22° C. and filtered. The fine solid was rinsed with hot methanol/methylene chloride and dried under reduced pressure, giving 7-methoxy-2-aminophenazine-5,10-dioxide (40% yield).

As will be described in the examples presented below, several compounds, which were presented in the chart above have been tested for their antimicrobial activity against a variety of bacteria. Of these compounds, only 2,3-dihydroxyphenazine-5,10-dioxide was found to be inactive against *P. gingivalis*. The following examples describe the claimed activities of the compounds of the invention and a manner and process of using the compounds, but are not intended to be construed as limiting. In each experiment, tetracycline, which is a currently preferred antibiotic for treatment of peridental infections, is tested simultaneously to provide a reference against which the substituted phenazine-5,10-dioxide compounds can be measured.

EXAMPLE 2

Minimum Inhibitory Concentration

Solutions of the agents were tested for activity against *Escherichia coli* strain DH5α by a zone inhibition method, and against *P. gingivalis* strain 2561 by addition to plating medium to determine minimum inhibitory concentrations (M/C). For the zone inhibition study, a suspension of *E. coli* was spread on the surface of an agar plate. A 3 mm diameter paper disk was placed on the seeded agar surface, and 10 μl of solution of each compound formulated at 1 mg/ml was added to the disk. Plates were incubated overnight at 37° C. The radius of the zone of inhibition was measured from the center of the disk to the edge of the *E. coli* bacterial lawn. For determination of MIC, drug solutions were mixed with plating medium to produce a range of final drug concentrations. Media with drug were plated in the wells of 24-well plates. A drop of bacterial suspension containing 2–5× 10$^2$CFU *P. gingivalis* was placed on each well. Plates were incubated 1 week in an anaerobic chamber at 37° C. The MIC was scored as the drug concentration that resulted in complete inhibition of bacterial growth. The results of both assays are summarized in Table 1.

TABLE 1

Clear Zone (mm) and MIC values (µg/ml)

| Compound | E. coli Clear Zone (mm) | P. gingivalis MIC (µg/ml) |
|---|---|---|
| phenazine-5,10-dioxide | 19 | 0.063 |
| 2-methylphenazine-5,10-dioxide | 19 | 0.004 |
| 2-hydroxyphenazine-5,10-dioxide | 15 | 0.016 |
| 2,3-dihydroxyphenazine-5,10-dioxide | inactive | inactive |
| 2-aminophenazine-5,10-dioxide | 32 | 0.002 |
| 2-hydroxy-3,4-iminopropylphenazine-5,10-dioxide | 17 | 0.031 |
| Tetracycline | 10 | 0.5 |

With the exception of 2,3-hydroxyphenazine-5,10-dioxide, the activities of the phenazine-5,10-dioxides were more potent against *E. coli* than was Tetracycline. Also, when the activities of the compounds were compared on a weight-concentration basis against the gram-negative obligate anaerobe *P. gingivalis*, the phenazine-5,10-dioxide compounds, except 2,3-hydroxyphenazine-5,10-dioxide, were more potent than Tetracycline. In the cases of the most active compounds tested in the example, 2-aminophenazine-5,10-dioxide and 2-methylphenazine-5,10-dioxide, activity was more than 100-fold greater than Tetracycline.

The molecular weight of the N,N'-dioxides of phenazine start at 212 g/mol, while Tetracycline is significantly larger at 442 g/mol. Because the molecular weights of the different compounds being compared vary widely, it may be more meaningful to compare potencies on a molar basis. These results are summarized in Table 2.

TABLE 2

MIC values (µM)

| Compound | P. gingivalis MIC (µM) |
|---|---|
| phenazine-5,10-dioxide | 0.296 |
| 2-methylphenazine-5,10-dioxide | 0.018 |
| 2-hydroxyphenazine-5,10-dioxide | 0.070 |
| 2,3-dihydroxyphenazine-5,10-dioxide | inactive |
| 2-aminophenazine-5,10-dioxide | 0.009 |
| 2-hydroxy-3,4-iminopropylphenazine-5,10-dioxide | 0.112 |
| Tetracycline | 1.13 |

From these values it becomes apparent that several embodiments of the invention (e.g., 2-aminophenazine-5,10-dioxide, 2-methylphenazine-5,10-dioxide, and 2-hydroxyphenazine-5,10-dioxide) have activity against this gram-negative anaerobic species in the nanomolar concentration range. This finding is entirely unexpected, especially in consideration of the result obtained with the currently preferred therapeutic agent Tetracycline, which demonstrated activity only at concentrations greater than 1 micromolar.

EXAMPLE 3

Antimicrobial Activity Against Bacterial Species

The substituted phenazine 5,10-dioxide identified as 2-aminophenazine-5,10-dioxide was tested for activity against a variety of bacterial species demonstrating differing microbiological characteristics such as gram designation (response to Gram's staining procedure), aerobic or anaerobic tolerance, presence of capsule, and presence of pigment. Drug solutions were mixed with plating medium to produce a range of final drug concentrations. Media with drug were plated in the wells of 24-well plates. A drop of bacterial suspension containing $2-5 \times 10^2$ CFU was placed on each well. Plates were incubated overnight at 37° C. The $IC_{90}$ was scored as the drug concentration that resulted in 90% inhibition of bacterial growth.

The concentration of the compound necessary to reduce viability of each micro-organism by 90% (inhibitory concentration 90%=$IC_{90}$) is reported in Table 3 as µg/ml. Bacterial strains are listed in order of decreasing susceptibility to 2-aminophenazine-5,10-dioxide.

TABLE 3

Activity of 2-aminophenazine-5,10-dioxide against Various Bacterial Species

| Species | $IC_{90}$ | Gr | an/aerobe | capsule | pigment |
|---|---|---|---|---|---|
| *Bacillus cereus* | 0.31 | + | aer | + | – |
| *E. coli* (strain B) | 0.31 | – (rfa) | fac | – | – |
| *Staphylococcus aureus* | 0.62 | + | fac | ± | – |
| *Corynebacterium xerosis* | 1.25 | + | fac | – | |
| *Streptococcus faecalis* | 5 | + | fac | – | |
| *Proteus mirabilis* | 5 | – | fac | – | – |
| *Micrococcus luteus* | 10 | + | fac | – | + |
| *Klebsiella pneumoniae* | 10 | – | fac | + | – |
| *Serratia marsescens* | 10 | – | fac | ± | + |

TABLE 3-continued

Activity of 2-aminophenazine-5,10-dioxide against Various Bacterial Species

| Species | $IC_{90}$ | Gr | an/aerobe | capsule | pigment |
|---|---|---|---|---|---|
| *Pseudomonas aeruginosa* | >10 | – | aer | ? | – |
| *Enterobacter cloacae* | >10 | – | fac | ± | – |

Notes:
Gr = gram-designation,
aer = obligate aerobe,
fac = facultative, and
rfa refers to a genetic variation from wildtype isolates which results in a greatly reduced outer cell wall structure in this strain.

From these data it appears that 2-aminophenazine-5,10-dioxide has relatively greater activity against gram-positive species than against gram-negative species. The only exceptions to this in the results above are 1) activity against the *E. coli* strain with a cell wall defect, which results in a phenotype intermediate between true gram-positives and gram-negatives; and 2) lack of activity against *M. luteus*, which contains carotenoid pigments that have been previously demonstrated to protect against other antimicrobial activities (e.g., Dahl et at., 1989). Antimicrobial activity was independent of the presence of a bacterial capsule and of the bacterial tolerance of anaerobic conditions.

suspensions of bacterial monocultures were added to the wells of 96-well plates. Cultures were incubated anaerobically overnight, and growth was assessed by measuring optical density at 650 nm. $IC_{50}$ values were determined as the compound concentration producing a turbidity reading equal to 50% of the maximum. Results are provided in Table 4. Again, results with Tetracycline are shown for comparison.

TABLE 4

Measured $IC_{50}$ Values (µg/ml) against anaerobic species

| Compound | *Fusobacterium nucleatum* | *Bacteroides fragilis* | *Bacteroides levii* | *Clostridium perfringens* | *Fusobacterium necrophorum* | *Peptostreptococcus anaerobius* | *Porphyromonas gingivalis* 2561 | *Porphyromonas gingivalis* RB-22D-1 |
|---|---|---|---|---|---|---|---|---|
| 2-amino-7-methoxy-phenazine-5,10-dioxide | ND | ND | ND | ND | ND | ND | 0.015 | 0.08 |
| phenazine-5,10-dioxide | 3.5 | 3 | 2.5 | 1 | 0.45 | 0.2 | ND | ND |
| 2-methylphenazine-5,10-dioxide | >10 | 7 | 1 | 1 | 1.5 | 0.2 | 0.16 | 0.35 |
| 2-hydroxyphenazine-5,10-dioxide | >10 | 5 | 0.2 | 1 | 0.45 | 0.45 | 0.62 | 0.22 |
| 2,3-dihydroxy-phenazine-5,10-dioxide | >10 | >10 | >10 | >10 | >10 | >10 | 5 | 2.0 |
| 2-aminophenazine-5,10-dioxide | 10 | 1 | 0.03 | 1 | 0.03 | 0.06 | 0.04 | 0.12 |
| 2-hydroxy-3,4-imino-propylphenazine-5,10-dioxide | >10 | 1 | 2 | 0.1 | 6.5 | 0.1 | 0.08 | 0.18 |
| Tetracycline | 0.16 | 0.1 | 0.1 | 0.06 | 0.03 | 0.03 | 0.02 | 0.06 |

ND: not done.

Based on the poor susceptibility of gram-negative bacterial species in general to 2-aminophenazine-5,10-dioxide, and the low antimicrobial activity against gram-negative and gram-positive pigmented species, it is extremely surprising that this compound is a very effective antimicrobial against a gram-negative, pigmented anaerobe such as *P. gingivalis*.

EXAMPLE 4

Antimicrobial Activity Against Anaerobic Bacterial Species

The concentrations of the various preferred substituted phenazine-5,10-dioxide compounds necessary to inhibit growth by 50% ($IC_{50}$ values) were determined for a variety of anaerobic bacterial species. Compounds were individually diluted into liquid growth media, which along with Susceptibilities of the various bacterial species to the antimicrobial activities of the compounds varied widely, with $IC_{50}$ values ranging from ng/ml levels to essentially ineffective. This confirms the relatively narrow spectrum of antimicrobial activity. For comparison, susceptibilities to the broad spectrum agent, Tetracycline, were consistently approximately equal to or less than 0.1 µg/ml.

Two *P. gingivalis* isolates were tested, and both were very susceptible to phenazine 5,10-dioxides. The species most susceptible to the substituted derivatives of phenazine 5,10-dioxide as a class were *P. gingivalis*, *P. anaerobius*, *F. necroforum*, and *B. levii*. These results demonstrate the potency of these agents against potential oral pathogens relevant to peridental infections. Several individual agents within the class of phenazine 5,10-dioxides were similarly potent or more potent than the preferred therapy in the current art, Tetracycline, against the susceptible species.

EXAMPLE 5

Anti-Collagenase Activity

Collagenase activity in the presence of the preferred compound 2-aminophenazine-5,10-dioxide and in the presence of Tetracycline were measured by incubating $^3$H-collagen with purified collagenase from *P. gingivalis* using increasing drug concentrations. After 24 h at 25° C., unhydrolyzed collagen fibers were removed from the mixture by centrifugation, and the specific activity of $^3$H in the supernatant quantified as a measure of hydrolyzed collagen. Percent inhibition was determined by subtracting the value in the presence of test compound from the control value, then dividing this quantity by the control value [(control−compound)/control×100]. Results are summarized in Table 5.

TABLE 5

2-aminophenazine-5,10-dioxide Anti-collagenase Activity

| Drug Concentration | % Inhibition | |
|---|---|---|
| | 2-aminophenazine-5,10-dioxide | Tetracycline |
| 1 µg/ml | 11.6 | 7.6 |
| 10 µg/ml | 47.3 | 31 |
| 50 µg/ml | 57.3 | ND |
| 100 µg/ml | 81.7 | 68 |

From these results it is clear that 2-aminophenazine-5,10-dioxide has significant unexpected anti-collagenase activity, with an $IC_{50}$ (concentration needed to inhibit activity by 50%) of a little more than 10 µg/ml. For comparison, the $IC_{50}$ of Tetracycline would be calculated at about 56 µg/ml.

EXAMPLE 6

Antimicrobial Activity Against *P. gingivalis* in Mice, Systemic Administration An animal model for testing the antimicrobial activity of the invention against *P. gingivalis* was conducted by inducing oral colonization of the microbe in BALB/c mice. Drug (2-methylphenazine-5,10-dioxide or Tetracycline) or control (2.5% cyclodextran) was administered intraperitoneally once each day for 25 days (2-methylphenazine-5,10-dioxide) or 40 days (Tetracycline). On the day following the last dose administration, the rear molars of the mice were swabbed and the swabs incubated in a growth medium to assess the presence of *P. gingivalis*. Mice were then sacrificed and jaw bones harvested for evaluation of bone loss. The results are reported in Table 6.

TABLE 6

Protection against Bone Loss by 2-methylphenazine-5,10-dioxide.

| Treatment Group | Bone Loss (BLU*) Average ± SD |
|---|---|
| No Bacterial Infection Sham Injection | 5.78** ± 0.41 |
| Bacterial Infection Sham Injection | 7.83 ± 0.46 |
| Bacterial Infection 5 mg/kg 2-methylphenazine-5,10-dioxide × 25 d | 6.27** ± 1.15 |
| Bacterial Infection 5 mg/kg Tetracycline × 40 d | 7.21 ± 0.73 |

*Bone Loss Units: 0.33 mm = 1 BLU.
**Significantly different from infected control at p < 0.05.

From these data it is apparent that inoculation with *P. gingivalis* induced bone loss in the study subjects. Treatment with the phenazine-5,10-dioxide derivative, 2-methylphenazine-5,10-dioxide, reduced the observed bone loss. Treatment with Tetracycline did not effect the bone loss even when administered for nearly twice as long.

It will be readily apparent to those skilled in the art that local application, i.e., oral, of the agent may result in higher drug levels at the site(s) of infection. Results with local application may reasonably be expected to mirror results with systemic administration.

EXAMPLE 7

Toxicity of Substituted Phenazine-5,10-dioxide

The potential for toxic side effects following systemic administration similar to the method used in the efficacy study was investigated by administering the compound 2-methylphenazine-5,10-dioxide to mice either in single or multiple intraperitoneal (IP) injections. These results are summarized in Table 7.

TABLE 7

Assessment of 2-methylphenazine-5,10-dioxide Toxicity.

| Dose | Route | Vehicle | No. of Injections | Deaths | Other Signs of Toxicity |
|---|---|---|---|---|---|
| 15 mg/kg | IP | 2.5% CD* | 17 | 0 | NONE |
| 30 mg/kg | IP | DMSO | 15 | 0 | NONE |
| 60 mg/kg | IP | 10% CD* | 1 | 0 | NONE |

*Cyclodextrin

It is apparent from these results that the phenazine-5,10-dioxide derivative, 2-methylphenazine-5,10-dioxide, was non-toxic, even at several times the dose found to provide significant therapeutic benefit.

Toxicity was also evaluated in rodents via intravenous (IV) and oral (PO) routes of administration across a range of dose levels. These results are summarized in Table 8.

TABLE 8

Assessment of 2-methylphenazine-5,10-dioxide Oral and IV Toxicity.

| Dose | Route | Vehicle | No of Administrations | Deaths | Other Signs of Toxicity |
|---|---|---|---|---|---|
| Mice | | | | | |
| 5 mg/kg | IV | 25% Cremaphor | 1 | 0 | NONE |
| 5 mg/kg | IV | 30% Encapsin CD | 1 | 0 | NONE |
| 5 mg/kg | IV | 100% DMSO | 1 | 0 | NONE |
| 30 mg/kg | IV | 10% Cremaphor | 1 | 0 | NONE |
| 40 mg/kg | IV | 25% Cremaphor | 1 | 0 | NONE |
| 50 mg/kg | IV | 30% Encapsin CD | 1 | 0 | Abnormal Clin Obs |
| 800 mg/kg | PO | 100% Cremaphor | 1 | 0 | NONE |
| 1000 mg/kg | PO | 100% Cremaphor | 1 | 1/2 | NONE |
| Rats | | | | | |
| 5 mg/kg | IV | 20% Cremaphor | 1 | 0 | NONE |
| 10 mg/kg | IV | 25% Encapsin CD/ 10% DMSO | 1 | 0 | NONE |
| 20 mg/kg | IV | 30% Encapsin CD | 1 | 0 | NONE |
| 50 mg/kg | PO | Water | 1 | 0 | NONE |
| 50 mg/kg | PO | 2% Brij 35/Water | 1 | 0 | NONE |
| 50 mg/kg | PO | 10% Brij 35/Water | 1 | 0 | NONE |
| 50 mg/kg | PO | 10% Brij 35/ Mineral Oil | 1 | 0 | NONE |
| 80 mg/kg | PO | 10% Cremaphor[1] | 1 | 0 | NONE |
| 100 mg/kg | PO | 110% Encapsin CD[2] | 1 | 0 | NONE |
| 100 mg/kg | PO | 10% Arlacel 83/ Corn Oil[3] | 1 | 0 | NONE |
| 100 mg/kg | PO | 100% PEG400[2] | 1 | 0 | NONE |
| 100 mg/kg | PO | 2% Brij 35[4] | 1 | 0 | NONE |
| 200 mg/kg | PO | 100% Cremaphor | 1 | 0 | NONE |

[1]F ~ 2%;
[2]F ~ 50%;
[3]F ~ 37%:
[4]F ~ 100%.

EXAMPLE 8

Bioavailibility of Substituted Phenazine-5,10-dioxide

The bioavailibility of orally delivered substituted phenazine-5,10-dioxides was measured because oral delivery also can comprise systemic administration. The bioavailibility was assessed for the phenazine-5,10-dioxide derivative, 2-aminophenazine-5,10-dioxide administered by oral gavage to rats. Vehicles and dose levels are detailed in Table 9. Calculations of bioavailability (F) following oral administration were made based on area under the curve (AUC) calculations and comparsion with intravenous administration. These results are summarized in Table 9.

TABLE 9

Availability of 2-aminophenazine-5,10-dioxide Administered Orally.

| Dose | Route | Vehicle | AUC* (µg · min/ml) | F** |
|---|---|---|---|---|
| 50 mg/kg | oral | water | 104.5 | 0.89 |
| 50 mg/kg | oral | 2% Brij35/water | 89.0 | 0.76 |
| 50 mg/kg | oral | 10% Brij35/water | 74.9 | 0.64 |
| 50 mg/kg | oral | 10% Brij35/ Mineral oil | 143.1 | 1.2 |
| 100 mg/kg | oral | Encapsin CD | 211.2 | 0.90 |
| 100 mg/kg | oral | PEG*** | 236.5 | 1.0 |

TABLE 9-continued

Availability of 2-aminophenazine-5,10-dioxide Administered Orally.

| Dose | Route | Vehicle | AUC* (µg · min/ml) | F** |
|---|---|---|---|---|
| 100 mg/kg | oral | Arlacel 83 | 157.6 | 0.67 |
| 60 mg/kg | oral | Cremaphor | 6.2 | 0.04 |

*Area under the curve of plasma level versus time after administration, calculated using the trapezoidal rule.
**F is Bioavailability, calculated compared to 10 mg/kg IV administration; AUC = 23.4 µg · min/ml.
***Polyethyleneglycol.

As shown in Table 9, several oral formulations, including simple dissolution in water, provided oral availability of this embodiment at the surprisingly high levels of approximately equal to or greater than 80%.

Other embodiments of the invention will be apparent to those skilled in the art from a consideration of this specification or practice of the invention herein disclosed. It is intended that the specification be construed as exemplary only, with the true scope and spirit of the invention represented by the following claims.

We claim:

1. Method of treating gram-negative anaerobic infection comprising the step of administering to an affected organism topically or systemically a therapeutically effective amount of phenazine-5,10-dioxide compound having the formula:

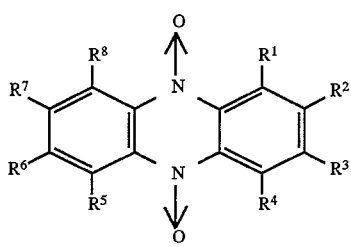

wherein $R_1$, $R_2$, $R_3$, $R_4$, $R_5$, $R_6$, $R_7$, and $R_8$ are independently H, $NH_2$, alkyl having 1–12 carbon atoms, lower alkoxy, lower alkyl amino, hydroxy, chloro, bromo, fluoro, iodo, or a pharmaceutically acceptable salt thereof, wherein two of $R_1$, $R_2$, $R_3$, and $R_4$ may be joined by an amino alkylene chain, provided that the phenazine-5,10-dioxide is not 2,3-dihydroxyphenzine-5,10-dioxide.

2. The method of claim 1 comprising the step of treating gram-negative anaerobic infection systemically by parenteral injection, or oral ingestion.

3. The method of claim 1 comprising the step of treating gram-negative anaerobic infection topically by administering to the oral cavity oral rinse solution, gingival paint, sublingual paste, dentifrice, sustained release oral lozenge, loaded dental floss fibers, or loaded polymer fibers.

4. The method of claim 1 wherein at least $R_1$, $R_5$, $R_7$, and $R_8$ are hydrogen.

5. The method of claim 1 wherein said lower alkyl amino is methylamino, ethylamino, n-propylamino, isopropylamino, n-butylamino, or t-butylamino.

6. The method of claim 1 wherein said lower alkoxy is methoxy, ethoxy, n-propoxy, isopropoxy, n-butoxy, or t-butoxy.

7. The method of claim 1 wherein said phenazine-5,10-dioxide compound is 2-aminophenazine-5,10-dioxide.

8. The method of claim 1 wherein said phenazine-5,10-dioxide compound is 2-methylphenazine-5,10 dioxide.

9. The method of claim 1 wherein said phenazine-5,10-dioxide compound is 2-hyroxyphenazine-5,10-dioxide.

10. The method of claim 1 wherein said phenazine-5,10-dioxide compound is 3,4-imminopropylphenazine-5,10-dioxide.

11. The method of claim 1 wherein said phenazine-5,10-dioxide compound is phenazine-5,10-dioxide.

12. The method of claim 1 wherein said phenazine-5,10-dioxide compound is 2-amino-7-methoxyphenazine-5,10-dioxide.

13. The method of claim 1 wherein said gram-negative anaerobic infection is an infection of peridental tissues.

* * * * *